US012594059B2

(12) United States Patent (10) Patent No.: US 12,594,059 B2
Mischi et al. (45) Date of Patent: Apr. 7, 2026

(54) QUANTITATIVE ANALYSIS OF UTERINE SPATIOTEMPORAL MOTION PATTERNS AND COORDINATION

(71) Applicants: TECHNISCHE UNIVERSITEIT EINDHOVEN, Eindhoven (NL); GYNAECOLOGIEPRAKTIJK B.C. SCHOOT B.V., Eindhoven (NL)

(72) Inventors: Massimo Mischi, Eindhoven (NL); Benedictus Schoot, Eindhoven (NL)

(73) Assignees: TECHNISCHE UNIVERSITEIT EINDHOVEN, Eindhoven (NL); GYNAECOLOGIEPRAKTIJK B.C. SCHOOT B.V., Eindhoven (NL)

( * ) Notice: Subject to any disclaimer, the term of this patent is extended or adjusted under 35 U.S.C. 154(b) by 493 days.

(21) Appl. No.: 18/011,369

(22) PCT Filed: Jun. 18, 2021

(86) PCT No.: PCT/EP2021/066709
    § 371 (c)(1),
    (2) Date: Dec. 19, 2022

(87) PCT Pub. No.: WO2021/255283
    PCT Pub. Date: Dec. 23, 2021

(65) Prior Publication Data
    US 2023/0233189 A1     Jul. 27, 2023

Related U.S. Application Data

(60) Provisional application No. 63/041,246, filed on Jun. 19, 2020.

(51) Int. Cl.
    A61B 8/00     (2006.01)
    A61B 5/00     (2006.01)
    A61B 8/08     (2006.01)
    G06T 7/00     (2017.01)

(52) U.S. Cl.
    CPC .......... *A61B 8/5223* (2013.01); *A61B 5/4356* (2013.01); *A61B 8/085* (2013.01); *G06T 7/0012* (2013.01)

(58) Field of Classification Search
    None
    See application file for complete search history.

(56) References Cited

U.S. PATENT DOCUMENTS

2016/0278688 A1     9/2016  Pierzynski et al.

OTHER PUBLICATIONS

Huang Y et al. "Quantitative Ultrasound Imaging Characterization of Uterine Peristaltic Waves" 2018 IEEE International Ultrasonics Symposium, Oct. 22, 2018, pp. 1-4.

(Continued)

*Primary Examiner* — Lennin R Rodriguezgonzalez
(74) *Attorney, Agent, or Firm* — Casimir Jones, S.C.; Robert A. Goetz

(57) ABSTRACT

Image analysis method for quantitative assessment of a degree of coordination of uterine motion, comprising: obtaining a recording of a uterus; tracking, in the recording, at least two propagation waves of uterine motion in at least two different regions of the uterus and/or on at least two different times; and determining the degree of coordination of the uterine motion based on a similarity measure of at least two characteristics of the at least two propagation waves.

20 Claims, 10 Drawing Sheets

(56)             References Cited

OTHER PUBLICATIONS

Sammali F et al. "Prediction of embryo implantation by machine learning based on ultrasound strain imaging" 2019 EEE International Ultrasonics Symposium, Oct. 6, 2019, pp. 1141-1144.

Huang Y et al. "Quantitative Motion Analysis of the Uterus by Optical Flow and Two-dimensional Strain Mapping" 2018 IEEE International Symposium on Medical Measurements and Applications, Jun. 11, 2018, pp. 1-5.

Sammali F "Measurement of the electromechanical uterine activity in the non-pregnant human uterus" PHD Thesis, Nov. 4, 2019, retrieved from the Internet: url: https://pure.tue.nl/ws/files/138191977/20191104_Sammali.pdf.

Long Y et al. "Identificiation and characterization of uterinemicroperistalsis in women undergoing in vitro fertilization and embryo transfer via dynamic ultrasound features" Archives of Gynecology and Obstetrics, Springer Verlag, vol. 300, No. 6, Oct. 23, 2019, pp. 1729-1739.

International Search Report & Written Opinion, Application No. PCT/EP2021/066709, mailed Oct. 4, 2021, 16 pages.

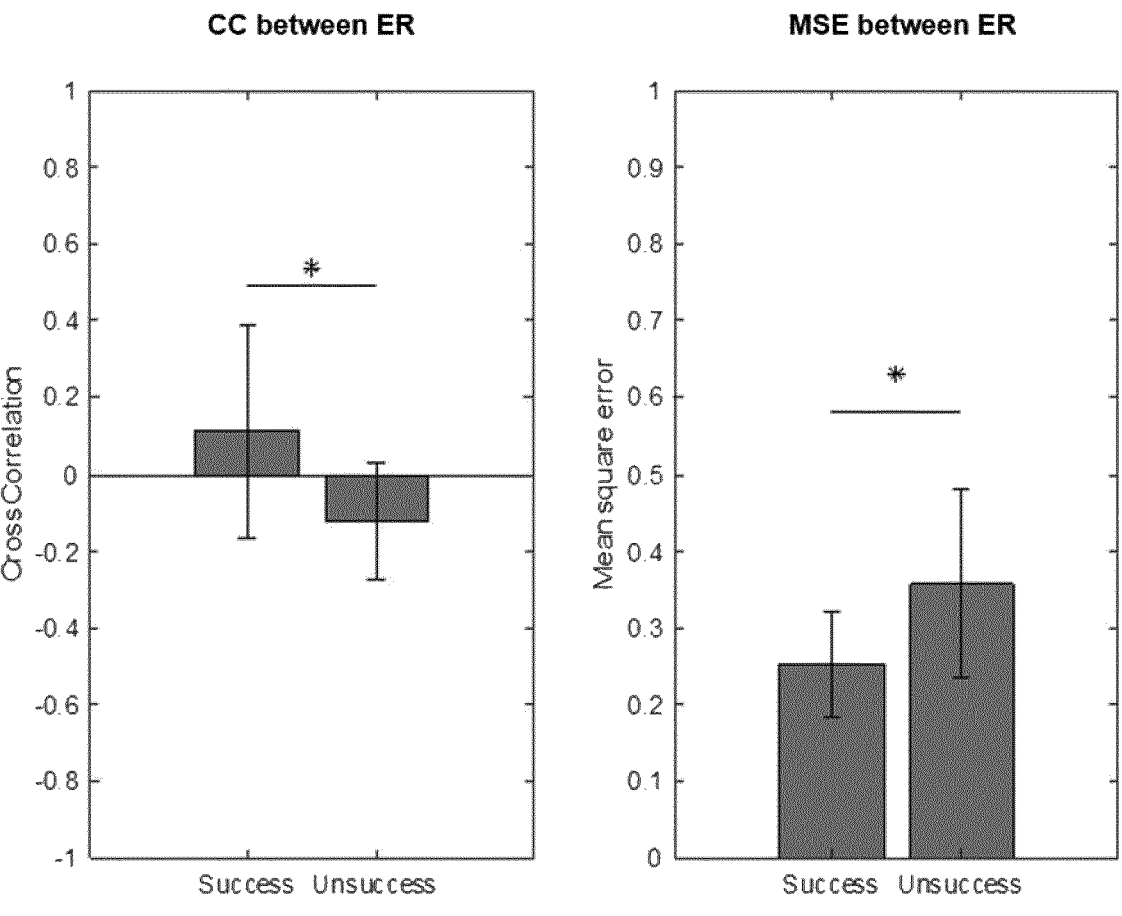
Fig. 5A                                    Fig. 5B

QUANTITATIVE ANALYSIS OF UTERINE SPATIOTEMPORAL MOTION PATTERNS AND COORDINATION

FIELD OF THE INVENTION

The invention relates to image analysis methods and systems for quantitative assessment of the degree of coordination of uterine motion. In addition, it relates to a computer program product for such quantitative assessment.

BACKGROUND OF THE INVENTION

Worldwide, approximately one in six couples experience infertility problems during their reproductive ages (from 20-44 years old). One possible way out for those infertile couples is to seek assisted reproductive technologies, such as in-vitro fertilization (IVF). In 2008, IVF represented the last resort for over 2.5 million couples in Europe. Meanwhile, in the last decade, the number of IVF cycles performed every year increases by over 20%. However, the success rate of IVF treatment remains below 30%, with only a 4% increment.

An IVF cycle involves the preparation of the subject with hormones, after which a number of eggs are picked up and fertilized in vitro. The resulting embryos are then transferred back into the uterine cavity. Successful implantation of the embryo in the uterine wall leads to pregnancy.

Dysfunction of uterine contractility has been indicated as one of the possible reasons hampering the success of the embryo implantation. The uterine body has three parts, an outside serosal layer, an inner lining called endometrium, and an intermediate muscle layer called myometrium, as shown in FIG. 1. Uterine contraction (UC), which results from uterine muscle shortening, was first mentioned in a non-pregnant uterus by Dickinson in 1937, based on bimanual palpation. UC mostly occurs around the endometrium, acting as a wave propagating along the endometrium lining. The resulting uterine deformation (motion) is also known as uterine peristalsis (UP). Due to the influence of hormone levels, both the UC and UP patterns change in terms of direction, frequency, velocity, and amplitude during different phases of the menstrual cycle. In particular, during the ovulation phase, when mature eggs are released from the ovary, opposing contraction waves are often generated to keep the eggs inside the endometrial cavity, waiting for fertilization. However, also women suffering from infertility problems are very likely to suffer from uterine disorders, such as endometriosis and adenomyosis, or endocrine effects, which can affect UP and hamper embryo implantation.

Therefore, reliable assessment of the uterine activity outside pregnancy can be expected to provide valuable insight into the influence of UP on IVF failure.

Currently, most of the assessment and characterization on UC and UP are based on qualitative measurements by visual inspection of transvaginal ultrasound (TVUS) recordings. However, visual characterization of the uterine activity is rather challenging and subjective, especially during the late luteal phase of the menstrual cycle, or right before embryo transfer during IVF treatment, where the uterus is expected to be quieter compared to other phases.

It has been shown that three medical professionals share only slight agreement on the direction and timing of the UP by visual inspection of 80 TVUS recordings. In other words, the lack of an objective and quantitative analysis of uterine contractility limits the ability to characterize UC and improve the success of an IVF cycle. The present invention addresses at least some of these shortcomings.

SUMMARY OF THE INVENTION

One of the objects of the invention is to provide for quantitative assessment of a degree of coordination of uterine motion.

A first aspect of the invention provides an image analysis method for quantitative assessment of a degree of coordination of uterine motion, comprising:

obtaining a recording of a uterus;

tracking, in the recording, at least two propagation waves of uterine motion in at least two different regions of the uterus and/or on at least two different times; and determining the degree of coordination of the uterine motion based on a similarity measure of at least two characteristics of the at least two propagation waves.

Various embodiments are defined in the appended dependent claims.

It is to be noted that the at least two propagation waves may be in at least two different regions of the uterus at the same time, or may be in the same region of the uterus on at least two different times, or may be in at least two different regions of the uterus on at least two different times. This may be indicated in the present disclosure as "at least two propagation waves of uterine motion in at least two different regions of the uterus and/or on at least two different times".

In an embodiment, the at least two characteristics comprise any of the following respective characteristics of the at least two propagation waves: direction; dominant direction; velocity; amplitude; and phase.

In an embodiment, the method comprises:

determining a measure of spread in the at least two characteristics over at least one of time and space.

In an embodiment, the tracking comprises selecting tracing markers in the recording using semi-automatic computer assistance such that subsequent tracing markers are substantially equidistant.

In a further developed embodiment, the tracing markers are selected in accordance with an anatomical feature of the uterus, preferably along an anterior side and along a posterior side of the endometrium.

In an embodiment, the method comprises compensating motion of the tracing markers by:

selecting a set of tracing markers from among the tracing markers in a frame of the recording;

determining a fitting curve based on the selected set of tracing markers;

determining translation and rotation of the fitting curve;

compensating coordinates of the tracing markers in subsequent frames of the recording based on the determined translation and rotation.

In an embodiment, the at least two propagation waves are tracked using any one of the following motion estimation techniques: block matching; optical flow; and optical flow including iterative spatial warping.

In a further developed embodiment, the iterative spatial warping comprises combining optical flow from a current frame to a first frame later than the current frame with optical flow from the current frame to at least one second frame later than the first frame.

In an embodiment, the similarity measure is determined using one or more of the following similarity measures: cross correlation; coherence; mean square error; mutual information; and Hausdorff distance.

In an embodiment, the method further comprises:

representing the at least two propagation waves in a frequency domain, preferably using a fast Fourier transform;

determining a first sum of spectral energies from a first quartile of the at least two propagation waves represented in the frequency domain, as an energy of cervix-to-fundus propagation;

determining a second sum of spectral energies from a second quartile of the at least two propagation waves represented in the frequency domain, as an energy of fundus-to-cervix propagation; and based on the first sum and the second sum, determining a ratio of the cervix-to-fundus propagation to the fundus-to-cervix propagation in order to determine a dominant direction of the at least two propagation waves.

In an embodiment, the method comprises:

determining whether or not the at least two propagation waves are substantially symmetric regarding the at least two characteristics with respect to at least one symmetry axis of an anatomical feature of the uterus, preferably with respect to an endometrium of the uterus; and outputting the result of the determining whether or not the at least two propagation waves are substantially symmetric, as a measure for expected success of fertilization of the uterus.

In an embodiment, the method comprises filtering out, with a bandpass filter, uterine motion components due to other sources than the uterus; wherein the other sources include at least one of: different organs than the uterus, such as bowels and/or a bladder; and acquisition motion including any one or more of: a heartbeat; a respiration; and a recording probe movement.

In an embodiment, the recording is of any one of the following types: two-dimensional, 2D, ultrasound; three-dimensional, 3D, ultrasound; magnetic resonance; and X-ray imaging. In the same embodiment or in a related embodiment, the recording spans at least a time period of 20 seconds, preferably 2 minutes, more preferably 4 minutes. Advantageously, 20 seconds may suffice to capture at least a workable part of at least one contraction of the uterus; 2 minutes may suffice to more reliably capture at least one contraction; and 4 minutes may suffice to more reliably capture a plurality of contractions in order to increase accuracy.

A second aspect of the invention provides a computer program product comprising a computer readable medium storing instructions configured for, when executed on a processor, causing the processor to perform the method of any above embodiment.

The skilled person will understand that considerations applying to the method apply analogously to the computer program product, mutatis mutandis.

A third aspect of the invention provides an image analysis system for quantitative assessment of the degree of coordination of uterine motion, comprising a processor and a memory storing instructions configured for, when executed on the processor, causing the processor to perform the method of any one of the above embodiments.

The skilled person will understand that considerations applying to the method apply analogously to the system, mutatis mutandis. In particular, instructions on memories of embodiments of the system may further comprise additional instructions analogous to the various embodiments of the above-described method.

Furthermore, the skilled person will understand that the system may be implemented using generic computer hardware, or using custom hardware, or using a combination of the two. Moreover, any suitable function or logical component of the system may be implemented using software, in addition to components, if any, that are implemented in hardware.

BRIEF DESCRIPTION OF THE DRAWINGS

These and other aspects and considerations of the invention will be more fully understood with the help of the embodiments described below and of the appended drawings, in which:

FIGS. 5A-B schematically show according to an exemplary embodiment of the invention bar plots (5A) representing the statistics of the coordination measurements in 16 IVF patients prior to embryo transfer;

DETAILED DESCRIPTION

Figure 1:
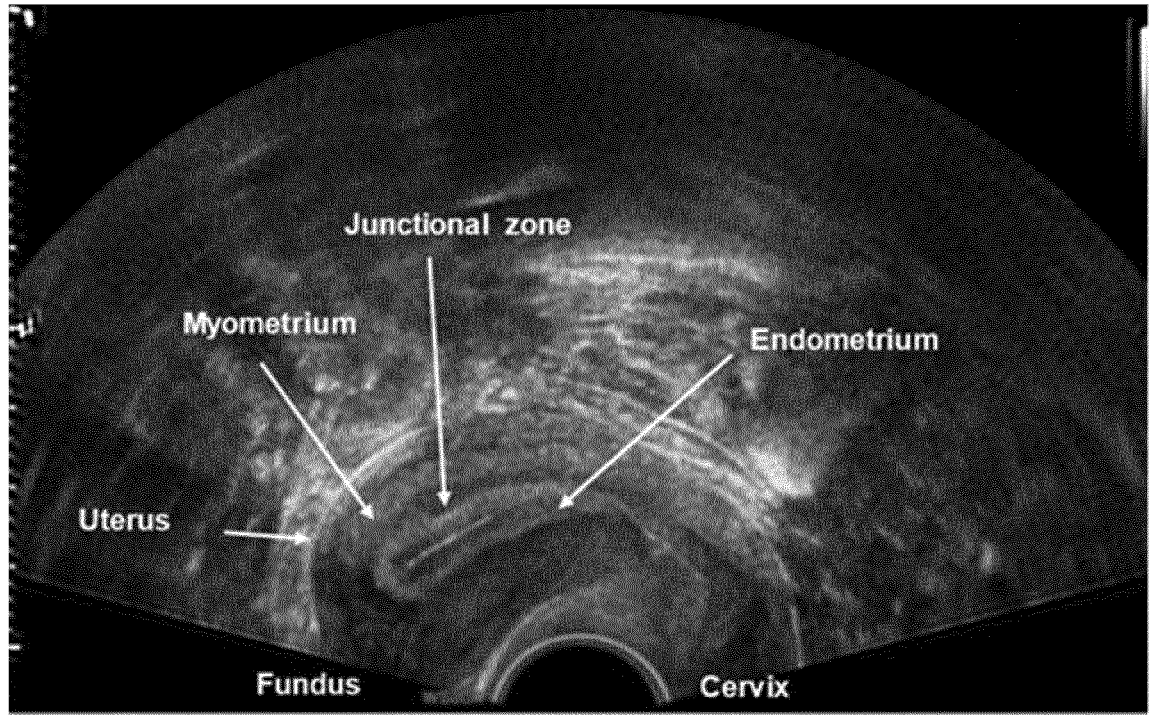
FIG. 1 schematically shows according to an exemplary embodiment of the invention an acquired US frame from an in-vivo recording during LF phase, illustrating several anatomical features of a uterus.
Figure 2:
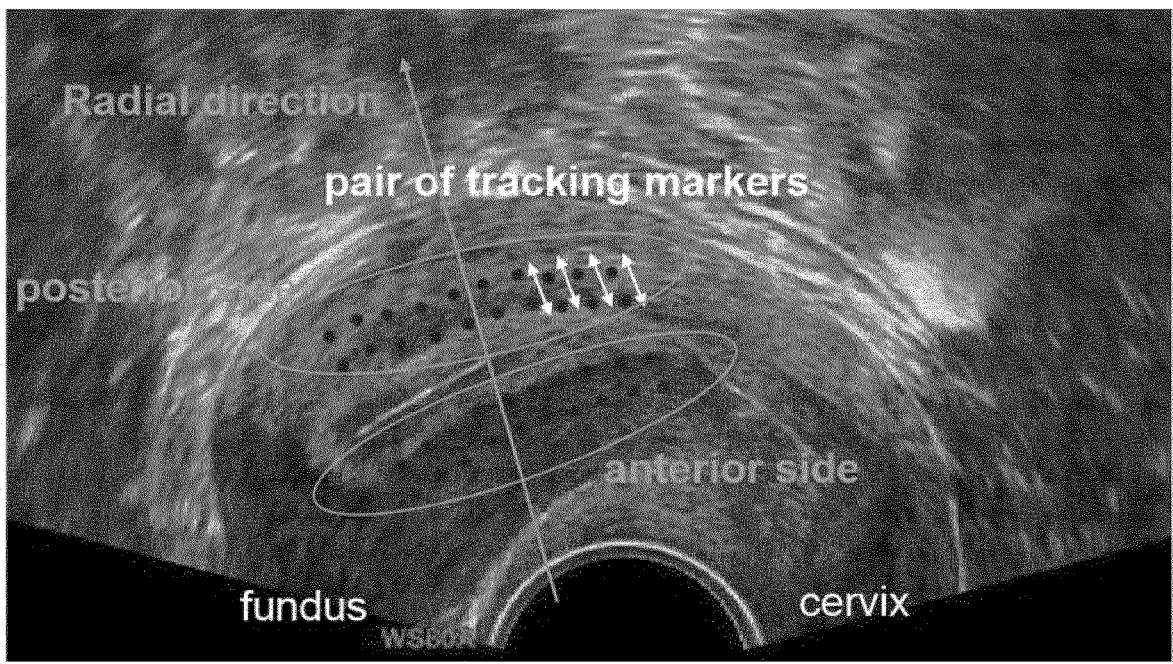
FIG. 2 schematically shows according to an exemplary embodiment of the invention tracing markers (TMs) positioned in 2D ultrasound.

It is an object of the invention to provide an image analysis method for quantitative assessment of the degree of coordination of uterine motion. The invention further aims to provide devices and systems related thereto to efficiently perform the image analysis. Further embodiments include devices and systems integrating image hardware devices or systems with the image analysis method. Yet further embodiments include computer hardware and software technology enabling the implementation of the image analysis method. To this end, motion tracking techniques may be employed to extract the uterine motion and strain from 2D or 3D video recordings. Several imaging technologies may be employed, ranging from ultrasound to magnetic resonance up to X-ray imaging. Uterine motion and strain may be recorded in space and time during one or multiple uterine peristaltic movements (also referred to as contractions). In particular, movement and strain (radial, circular, or longitudinal) may be recorded relative to the uterine anatomy, i.e. relative to an anatomical feature of the uterus. FIG. 2 schematically shows according to an exemplary embodiment of the invention tracing markers (TMs) positioned in 2D ultrasound. The markers may be positioned along the anterior and posterior sides of the endometrium in order to analyse the coordination of radial strain along the longitudinal direction. This transvaginal recording was acquired in a healthy volunteer during late follicular phase. As an example, as shown in FIG. 2, radial strain may be assessed around to the endometrial line along the longitudinal direction of the uterus. Based on the spatiotemporal evolution of the peristaltic movement relative to the uterine anatomy, embodiments of the invention may be related to a method for the assessment of the degree of coordination or dyscoordination of the peristaltic waves.

One approach may be to evaluate the similarity in the time evolution of the dominant direction of propagation between different regions of the uterus. As an example, between the anterior and posterior wall. Likewise, the velocity itself, in the different directions, may also be evaluated for its similarity in different regions. Several similarity measures may be adopted, such as correlation, coherence, mean square error, and mutual information. Besides propagation direction, the spatial distribution of amplitude and phase of the peristaltic waves in different regions of the uterus may also be considered to assess the degree of similarity. A global coordination index may be extracted by evaluation of the spread (e.g. standard deviation) in direction, amplitude and phase of the peristaltic waves across the uterus. Coordinated contractions that are symmetric with respect to the uterine anatomy (e.g. radial symmetry about the endometrial line) may lead to efficient peristalsis and stronger micro-streams within the endometrial space. This phenomenon may have an impact on the uterine function and the ability to favour embryo implantation as well as uterine emptying during the menstrual phase. Stability of a certain motion condition and uterine behaviour may be evaluated by assessment of the variance of the estimated index over time.

In one embodiment, the invention relates to a method for the assessment of uterine coordination by spatiotemporal analysis of strain in the longitudinal, radial and circular direction of the uterus, where such strain may be represented by a harmonic wave that propagates along the uterus. Coordination may be defined as the similarity of the characteristics of such wave in different regions of the uterus. The considered characteristics may comprise the time evolution of the direction of propagation, phase, and amplitude, in an arbitrary time interval that has at least one cycle (period) of such wave. The adopted similarity measures may include correlation, spectral coherence, mutual information, and squared error. At a given time instant, a coordination index may be extracted by assessment of the spread of the measured wave characteristics over a region of the uterus up to the entire uterus. The variance of these indices over time may also be assessed as measure of stability of the uterus or a region of the uterus in certain motion condition.

Various embodiments of this invention are directed to dedicated ultrasound (US) speckle tracking for quantitative analysis of uterine motion. In these embodiments, a quantitative assessment of the uterine activity may be provided focusing on the propagation pattern of UP along the uterus during a natural menstrual cycle as well as during an IVF cycle.

In particular, next to the estimation of velocity and direction of the propagating waves (e.g. Huang et al. Quantitative ultrasound imaging and characterization of uterine peristaltic waves, IEEE IUS, Kobe (Japan), Oct. 22-25, 2018), the present invention considers the spatiotemporal coordination of UP, which may provide a powerful descriptor of the ability of the uterus to act either in favour of or against embryo implantation.

To quantify UC, it is preferred to first assess uterine motion throughout the ultrasound (US) recording. In the field of US-based speckle tracking, two major motion estimation approaches are known, namely, block matching (BM) and optical flow (OF). BM segments the image into blocks and seeks the best matches of these blocks in subsequent frames based on a chosen matching criterium. On the other hand, OF is a pixel-to-pixel gradient approach which estimates the velocity of the target object between two subsequent frames. For preferred embodiment of the present invention, OF may be chosen over BM due to its higher sensitivity to sub-pixel motion. Moreover, tracking accuracy of OF may be further improved by implementing an iterative spatial warping method. The adopted OF method may first be optimized and then validated in-vitro using a dedicated setup with human ex-vivo uterus.

Uterine Motion Tracking

One embodiment of the invention may be based on 2D ultrasound (US) imaging of the uterus for 2 to 4 minutes. US speckle is caused by the interference of the backscattered ultrasound energy received by the transducer. Tissue typically forms a unique speckle pattern which may be tracked over time. In other words, tissue motion may be recovered by tracking the movement of the speckle pattern. Block matching (BM) and optical flow (OF) are two widely used speckle tracking algorithms to track tissue motion.

The tracking result from BM is limited to an integer numbers of pixels, thus the accuracy is bounded to the pixel size of the US images. On the other hand, OF does not have such restriction. As the highest endometrial wave velocity observed was less than 2 mm per second, being the acquisition frame rate and pixel size equal to 30 Hz and 0.065 mm, respectively, uterine motion was smaller than 1 pixel per frame. Therefore, OF may be more suitable to provide accurate tracking results.

The principle of OF is based on the assumption that the intensity, I, of a certain pixel located at (x, y, t) in space and time does not change after a displacement by $(\Delta x, \Delta y)$ in a period of $\Delta t$, i.e., $$I(x, y, t) = I(x + Dx, y + Dy, t + Dt). \tag{1}$$

Taylor expansion may be applied to the right-hand side of Eq. 1. Higher order terms of the expansion may be ignored under the assumption of small deviation in time and space between subsequent frames. The velocities of the moving pixel, v, in the x and y directions may thus be represented by the intensity gradients in the spatial and temporal domains as $$v_x \frac{\partial I}{\partial x} + v_y \frac{\partial I}{\partial y} + \frac{\partial I}{\partial t} \bigg| = 0. \tag{2}$$

To solve the above ill-conditioned equation, Lukas and Kanade proposed to estimate the motion of a block instead of a pixel under the assumption of constant flow within the block (Lucas et al., Iterative Image Registration Technique with an Application To Stereo Vision. Technical report, 1981). The velocities in both directions may then be obtained by least square estimation. After that, the pixel location in the target frame may be updated according to the estimated velocities.

The accuracy of OF may be further improved by applying an iterative refinement approach under the assumption of small motion. In a preferred embodiment, OF may first be applied to track the motion of a selected speckle pattern between the reference frame and the target frame. Based on an initial estimation $v_1$, the target frame may be warped by 2D interpolation. This way, the movement of the speckle pattern may be partly retrieved between the reference and the target frames. Then, in the second iteration, a new estimation of residual motion, $v_2$, may be derived between the reference and the warped target frames. This process may be applied iteratively until the residual motion $v_n$ converges to a very small value, or until it reaches a predefined maximum number of iterations N. The final estimation of the pixel motion, $v_{end}$, may then be calculated as the sum of the initial motion and all the residual motions, $$v_{end} = \sum_{n=1}^{N} v_{end}.$$

Apart from applying an iterative refinement, the choice of the block size may be relevant for OF to obtain accurate tracking results. If it is chosen too small, the tracking might become too sensitive to local motion and noise; if the block size is chosen too large, the hypothesis of constant flow might be violated. The optimization of the block size was carried out ex-vivo by means of a dedicated experimental setup proposed in Sammali et al. (Sammali et al., Dedicated Ultrasound Speckle Tracking for Quantitative Analysis of Uterine Motion Outside Pregnancy. IEEE Trans. Ultrason. Ferroelectr. Freq. Control, 66 (3): 581-590, March 2019). The optimized block size may be considered 41×41 pixels (around 2.6×2.6 mm²).

Anatomical Strain Framework

UP is often observed close to the endometrium in the junctional zone rather than in the myometrium. Tracing markers (TMs) may therefore be selected along the anterior and posterior sides of the endometrial cavity at the first frame of each US recording. A semi-automatic approach may be employed to guarantee the same distances between each pair of TM along the endometrium in the radial direction, as shown in FIG. 2. In this embodiment, the distance may be chosen as the optimal block size avoiding overlapping blocks, but other choices are possible as well, as long as the grid follows the uterine anatomy.

Figure 3A:
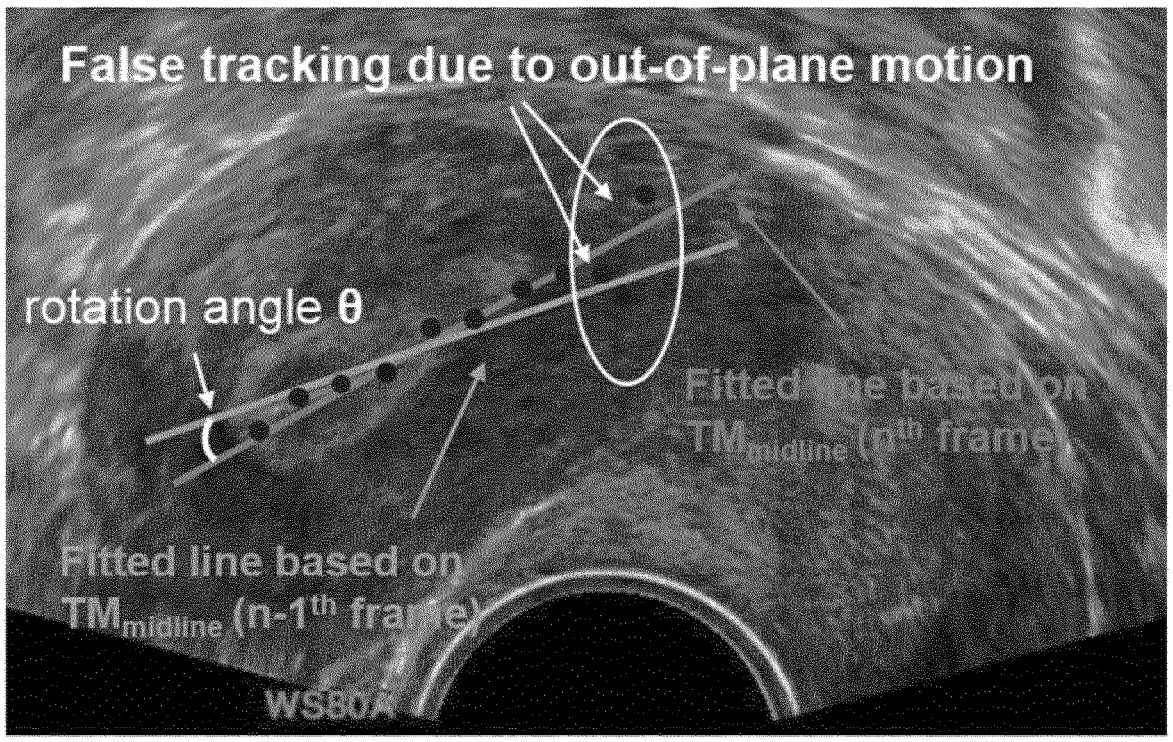
FIGS. 3A-B schematically show according to an exemplary embodiment of the invention (3A) compensation of motion.
Figure 3B:
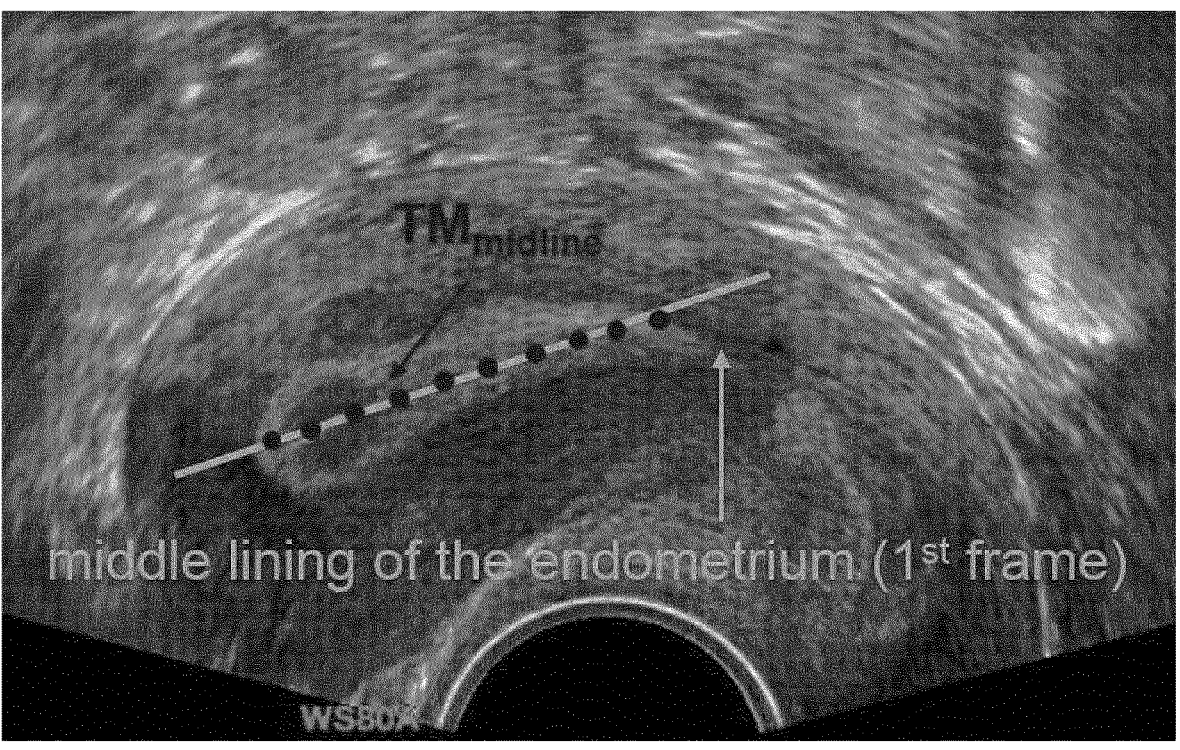

FIGS. 3A-B schematically show according to an exemplary embodiment of the invention (3A) compensation of motion; wherein 10 TMs$_{midline}$ are selected along the middle lining of the endometrium, and (3B) Out-of-plane (OOP) motion starts from the $n^{th}$ frame. Although speckle tracking fails with two TMs (pointed out with white arrow), the global rotation of the endometrium is still recovered by the fitted lines between subsequent frames, as will be explained below. OOP motion is a frequent phenomenon during 2D US recording in vivo. The occurrence of OOP motion is mainly caused by movement of the imaged target in the third dimension perpendicular to the observation plane. It can also be caused by the influence of probe motion and patient movement. Once OOP motion occurs, the speckle pattern being tracked tends to move out of the observation plane. The resulting decorrelation of the speckle pattern might lead to failure in speckle tracking. To mitigate the influence of OOP motion on the accuracy of 2D speckle tracking with in-vivo data, a two-step approach may be considered. In the first step, 10 tracking markers (TMs$_{midline}$) with isotropic distance may be selected along the middle lining of the endometrium, as shown in FIG. 3A; speckle tracking may be applied to TMs$_{midline}$ through the entire recording. The global translation of the endometrium ($x_t$; $y_t$) may be estimated by averaging the movement of TMs$_{midline}$ in the horizontal and vertical directions. After that, the rotation of the endometrium ($\theta_t$) may be estimated by linear fitting based on the coordinates of TMs$_{midline}$, as shown in FIG. 3B. This way, even if part of the endometrium is affected by OOP motion, the global (rigid) translation and rotation may still be recovered from the rest of the TMs$_{midline}$ which may not be affected by OOP motion.

Once global translation ($x_t$; $y_t$) and rotation ($\theta_t$) of the endometrium through the entire recording is obtained, the coordinates of the TMs may be updated for each frame as $$\begin{bmatrix} X_t \\ Y_t \end{bmatrix} = \begin{pmatrix} \cos(\theta_t) & -\sin(\theta_t) \\ \sin(\theta_t) & \cos(\theta_t) \end{pmatrix} \times \begin{bmatrix} X_{t-1} \\ Y_{t-1} \end{bmatrix} + \begin{bmatrix} x_t \\ y_t \end{bmatrix}, t = 2, \dots, N, \tag{3}$$

where N is the number of frames and ($X_1$; $Y_1$) represents the coordinates of the TMs selected in the first frame, relative to the uterine anatomy. In the second step, speckle tracking may be applied to the TMs accounting only for their displacement between subsequent frames relative to the original position, which was derived in Equation 3. Therefore, the TM position may not be updated by tracking, but may stay in the original anatomical position defined by ($X_1$; $Y_1$). As a result, speckle tracking may be applied only between two subsequent frames. This way, even if OOP motion caused decorrelation and poor tracking, the tracking error may remain limited between two frames without further accumulation. With this approach, tracking is performed for TMs representing consistent anatomical positions, enabling further interpretation of the results as associated to the uterine anatomy and geometry. When an US 3D acquisition is available, OOP motion may also be tracked and the tracking results may be more accurate. In fact, due to the relatively slow uterine motion, volume rates of typical 3D US acquisitions below 1 Hz may still be sufficient to meet Nyquist condition and perform accurate tracking of UP.

Radial Strain Rate Analysis

Strain rate imaging is a known approach for measuring regional or global deformation of the muscle. To characterize UP, a radial strain rate (RSR) may be derived from both the anterior and posterior sides of the endometrium. RSR may be calculated from the ratio between the variation in the distance between each pair of TMs in the radial direction, as shown in FIG. 2 and their original distance, given as $$RSR_t = \frac{D_t - D_{t-1}}{D_1 \Delta t}, t = 2, \dots, N, \tag{4}$$

where $D_t$ represents the absolute distance between each pair of TMs in the radial direction at the $t^{th}$ frame; $D_1$ is the original distance; $D_t$ is the time interval between two frames, and N is the total number of frames of the recording. By variations in the reference distance, alternative strain definitions may also be considered, based e.g. on the Lagragian (LS) and Eulerian (ES) strain:

$$LS = \frac{D_t - D_1}{D_1},$$

$$ES = \frac{D_t - D_{t-1}}{D_{t-1}}.$$

It can often be observed that UC is not the only source of motion influencing the movement of the endometrium in US recordings. Other motions, either originating from different organs, such as, bowels and bladder, or caused by heartbeat, respiration, and probe movement during the acquisition, may all be recorded as well during the US scan. Therefore, a bandpass filter may be applied to the RSR signals to remove the interference from these undesired motion sources. It is known that UC during a normal menstrual cycle varies from 0.5 to 4.1 contractions per minute, while during IVF treatment, UC appears to be more frequent due to the ovarian stimulation by hormones, resulting in a range from 0.5 to 5 contractions per minute. The cut-off frequencies of the bandpass filter may therefore be chosen according to these ranges, based on the intended application. Alternative pre-processing stages may also make use of singular value decomposition (SVD) filtering of the recorded US loops, focusing on the frequencies of interest.

Uterine Coordination

Based on RSR signals, a time-space representation of the UP may be created travelling along the endometrium. Clear propagation of UC from cervix to fundus (C2F) can be observed in FIG. 4A, and from fundus to cervix (F2C) in FIG. 4B. FIGS. 4A-D schematically show according to an exemplary embodiment of the invention (4A) a time-space representation of UP created by the RSR extracted from the anterior side of the endometrium from a healthy volunteer. This plot shows clear propagation C2F. (4B) Time-space representation of UP created by the RSR extracted from the posterior side of the endometrium from a healthy volunteer. This plot presents F2C propagation. (4C) Corresponding frequency-domain representation (k-space) of (a): dominant spectral peaks (marked with red points) are present in the first and third quartile representing C2F propagation. (4D) Corresponding frequency-domain representation (k-space) of (b): dominant spectral peaks (marked with red points) are present in the second and forth quartile representing F2C propagation.

Figures 4A, 4B:
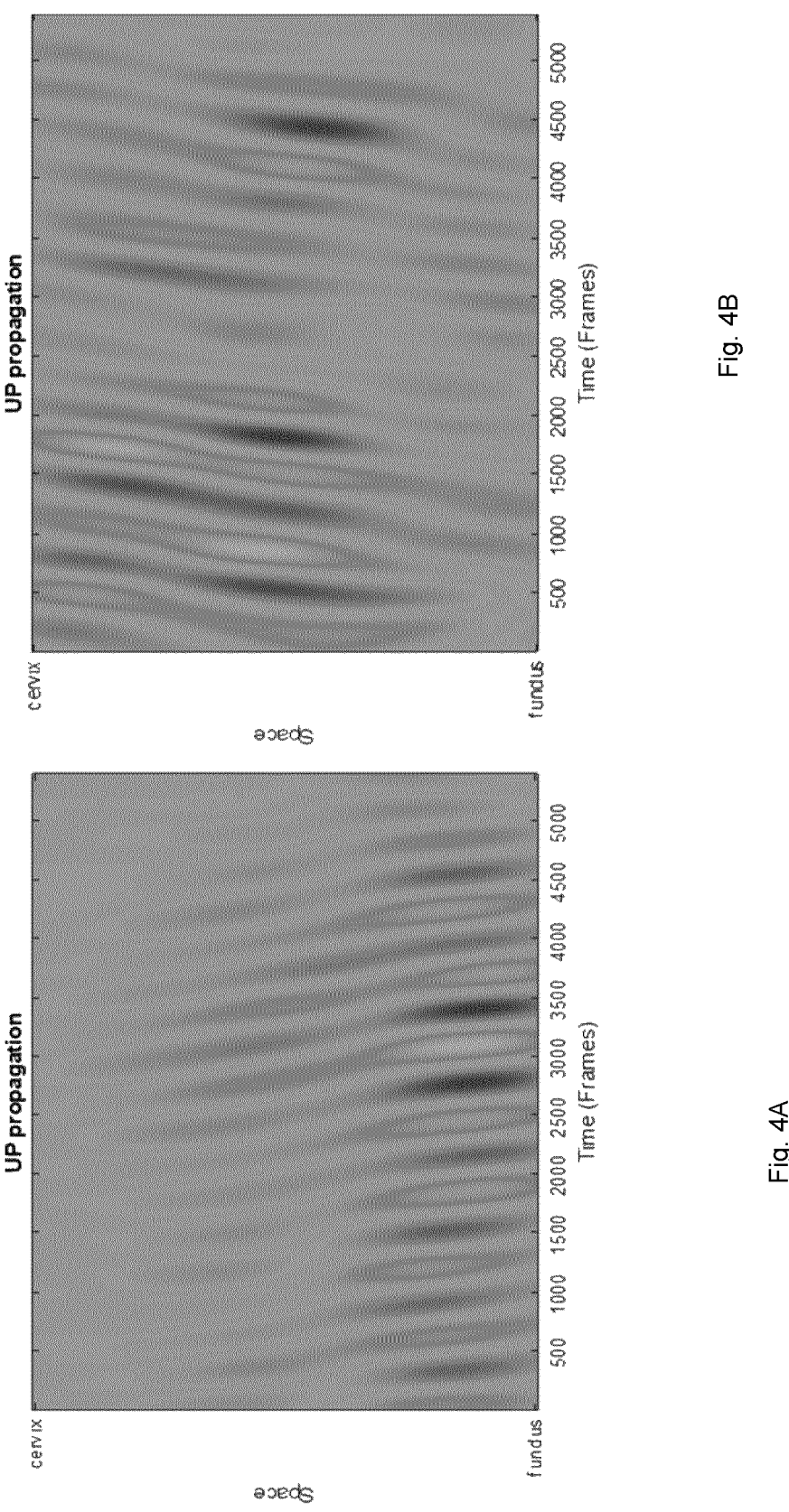
FIGS. 4A-D schematically show according to an exemplary embodiment of the invention (4A) a time-space representation of UP created by the RSR extracted from the anterior side of the endometrium from a healthy volunteer.
Figures 4C, 4D:
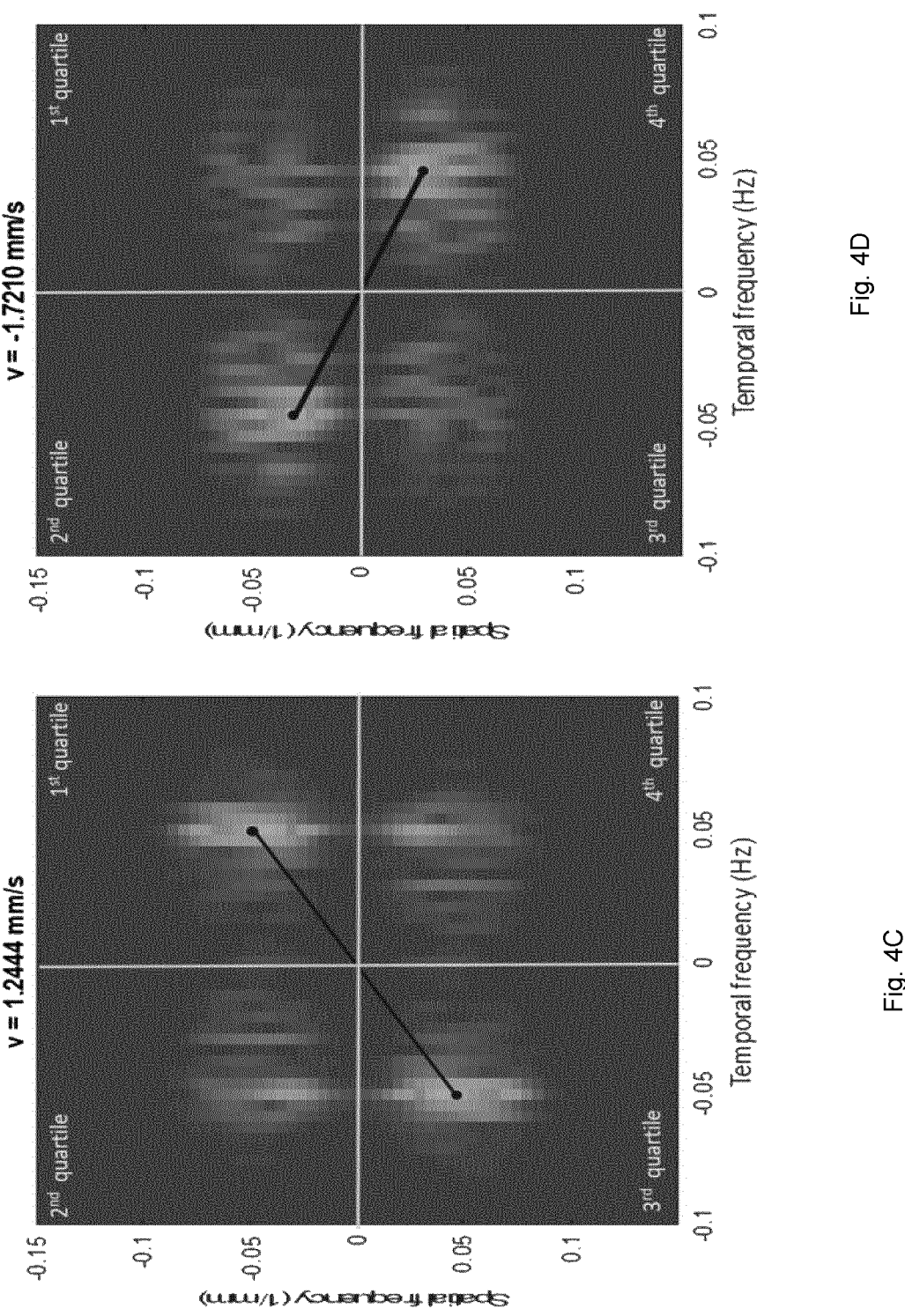

To estimate the velocity of the UP, two-dimensional fast Fourier transform may be applied to the spatiotemporal representation, resulting in a frequency representation in the k-space domain. FIG. 4C and FIG. 4D show the k-space representations corresponding to the examples shown in FIG. 4A and FIG. 4B. The temporal and spatial frequencies of the dominant peristaltic motion may be identified as the peaks of the spectrum. The velocity of such UP (in the longitudinal direction), $v_{UP}$, may be calculated as the ratio between the temporal frequency, $f_t$, and spatial frequency, $f_x$, as $$v_{UP} = \frac{f_t}{f_x} \qquad (5)$$

However, more complex UP patterns can sometimes be observed in practice. Opposing propagation, which shows both C2F and F2C propagation, can often be observed after ovulation to support embryo implantation; recoiling propagation, which includes reflection and superposition of multiple peristaltic waves can also be observed, as well as more complex propagation.

To estimate the UP velocity in more complex conditions, a moving window may be applied to segment the time-space representation over time. Within each segment, UP velocities in both C2F and F2C directions may be explicitly estimated from the peaks in the first quartile (representing UP traveling from C2F) and the second quartile (representing UP traveling from F2C) of the k-space representing the spatiotemporal frequencies. This way, the evolution of UP velocities in both directions may be obtained, advantageously providing a more comprehensive understanding of how UP propagation patterns evolve over time. In a preferred embodiment, the size of the moving window may be chosen as 600 frames (20 seconds) with a step size of 1 frame.

Next to absolute velocity, estimation of the direction of propagation may provide additional relevant information. This may be determined by the sign of $v_{UP}$. Propagation from C2F may be indicated by a positive sign while propagation from F2C may be indicated by a negative sign. However, such binary classification may not be suitable when a complex propagation pattern occurs. Therefore, an energy ratio (ER) metrics may be defined, wherein the sum of spectral energies may be extracted from the first quartile (E1) and the second quartile (E2), representing the energy of C2F and F2C propagation, respectively. This is given as $$ER = \frac{2E_1}{E_1 + E_2} - 1 \qquad (6)$$

The parameter ER, which is comprised between −1 and 1, may represent an index of UP coordination in time domain, advantageously providing a dominant direction of propagation at a given time. Coordinated motion may result in ER approaching either 1 (reflecting C2F propagation) or −1 (reflecting F2C propagation). In case of ER around zero, opposing propagation and standing waves may likely occur.

The fact that locally, e.g. along the anterior or posterior wall, UP shows a dominant direction, may not necessarily guarantee an effective peristaltic movement that is coordinated and generates microstreaming in the endometrial cavity. Simply focusing on the anterior and posterior walls, coordinated, effective peristalsis may require UC propagation on both sides of the endometrium to show the same direction at the same time. Especially during ovulation, it is believed to be important that muscles from both sides of the endometrium produce coordinated contractions to support embryo implantation. This way, similar ERs from both the anterior ($ER_{ant}$) and posterior ($ER_{pos}$) sides of the endometrium are expected. Similarity measures, namely, cross correlation (CC) and mean squared error (MSE), may be employed as cost functions to assess the spatiotemporal coordination of the UP.

FIGS. 5A-B schematically show according to an exemplary embodiment of the invention bar plots (5A) representing the statistics of the coordination measurements in 16 IVF patients prior to embryo transfer. Two groups were separated corresponding to successful (pregnancy at 11 weeks gestation, 7 patients) and unsuccessful (9 patients) IVF. The ER similarity between posterior and anterior uterine wall is presented in terms of cross correlation and mean square error. The bar plots show the mean (blue thick bar) and standard deviation (black thin bar). The asterisk (*) indicates significant difference (p<0.05) between the successful and unsuccessful groups. FIGS. 5A and 5B show the ability of CC and MSE between $ER_{ant}$ and $ER_{pos}$ to predict successful embryo implantation and pregnancy prior to embryo implantation in 16 patients undergoing IVF. Alternative similarity measures, based e.g. on statistical dependency and mutual information, may also be considered. Next to the dominant direction, represented by ER according to Equation 6, the absolute velocity in the different directions may also be evaluated for its similarity in different regions, advantageously providing alternative measures of coordination which are still related to the direction of propagation.

The above supports the principle wherein coordination may be interpreted as correlated propagation direction in different regions of the uterus. In an alternative embodiment, coordination may be derived by the spatial distribution of the phase of the peristaltic waves in a given time interval. In fact, neglecting its nonstationary nature (limiting the time interval by windowing) a peristaltic wave P(r, t), reflecting strain in a defined direction relative to the uterine anatomy (e.g., radial strain), may be represented as $$P(\underline{r}, t) = A(\underline{r})\cos(\omega t + \varphi(\underline{r})), \tag{7}$$

with r representing the spatial coordinates relative to the uterine anatomy, ω the time frequency, and φ the phase. In-phase radial motion may reflect coordination and effective peristalsis, while out-of-phase motion may reflect dyscoordination. In particular, 180-degree phase shift may represent snake-like motion, which can often be observed in the uterus and may influence embryo implantation. Therefore, the radial dispersion of the phase may represent an additional index of coordination. The standard deviation (spread) of the phase, φ(r), over a defined region, the entire organ, or about the endometrial line, may also be used as a global index of (dys)coordination. The same reasoning may be applied to the other wave parameters in Equation 7. The time stability of the uterine motion in a certain condition may be further evaluated by assessment of the standard deviation or the variance of the extracted index over time. Moreover, similar to the direction of propagation (ER), the time evolution of the parameters in Equation 7, such as A(r, t) and φ(r, t), may also be evaluated and the similarity in different regions assessed by the proposed similarity measures.

Figure 6A:
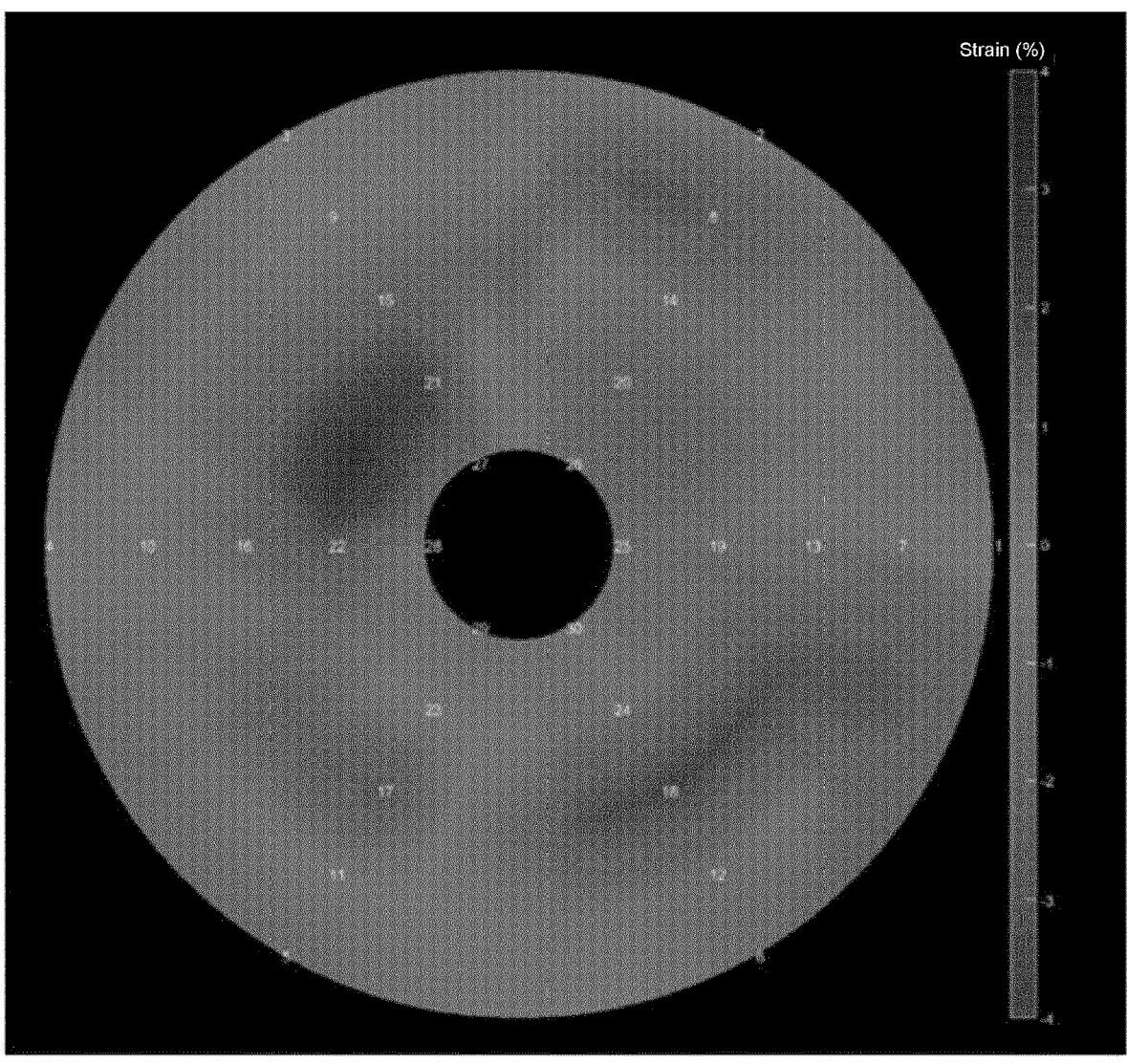
FIGS. 6A-B schematically show according to an exemplary embodiment of the invention a bull-eye plot (6Aa) and a 3D representation (6B) of a UP wave parameter.
Figure 6B:
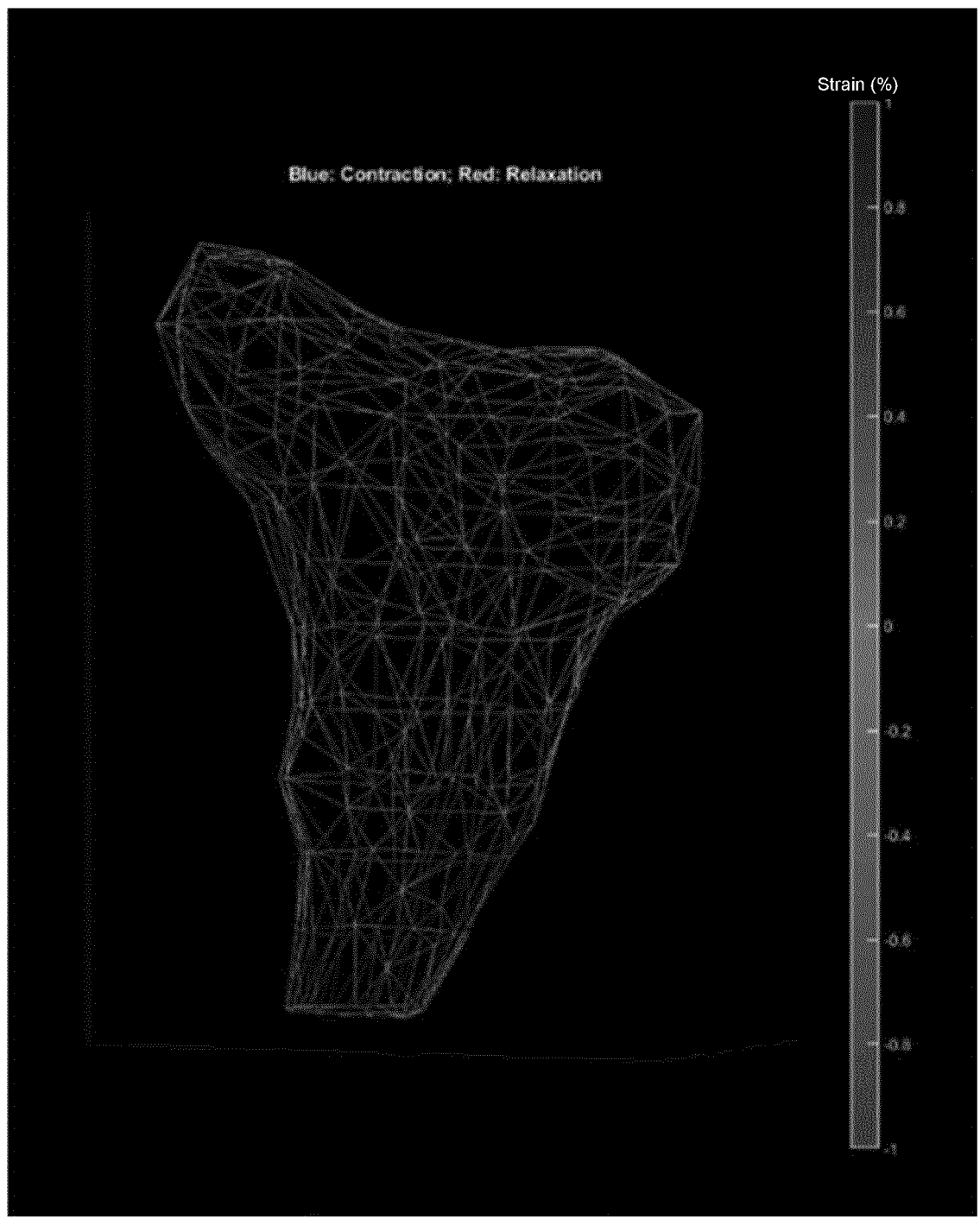

While the above-described embodiments use 2D ultrasound recording, more accurate information may advantageously be obtained by 3D ultrasound recording. The ER parameter may in that case be calculated for every region of the uterus, and a representation of the direction of propagation may be provided in a 3D spatial representation or by a bull-eye plot, developing from cervix to fundus and showing UP phase, amplitude, frequency, and direction (ER) in all radial segments of the uterus from cervix to fundus, as shown in FIG. 6A and FIG. 6B, which show a bull-eye plot (6Aa) and a 3D representation (6B) of a UP wave parameter. Global coordination may then be derived by the similarity of the extracted phase, direction, and amplitude of the peristaltic waves for each segment of the uterus. Isolated dyscoordinated regions may also be identified that show dyscoordinated motion patterns. Besides IVF, such a tool may prove valuable also for the diagnosis of uterine dysfunctions and pathologies, such as endometriosis, adenomyosis, myomas and sarcomas.

Figure 7A:
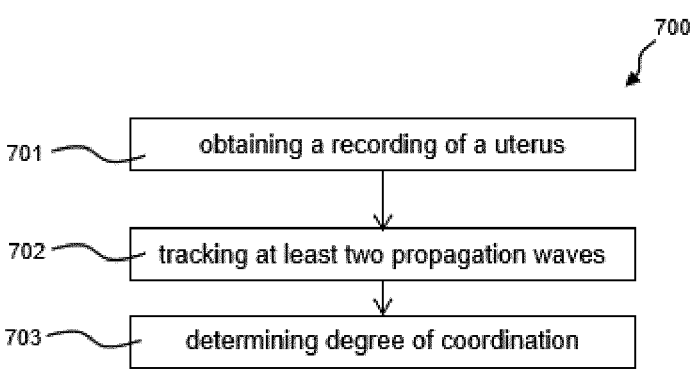
FIGS. 7A-B schematically illustrate an embodiment of a method according to the invention and an embodiment of a device according to the invention, respectively.
Figure 7B:
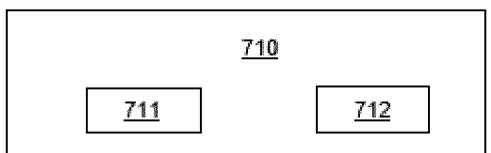

FIGS. 7A-B schematically illustrate an embodiment of a method according to the invention and an embodiment of a device according to the invention, respectively. The method 700 illustrated in FIG. 7A comprises the steps of: obtaining 701 a recording of a uterus; tracking 702, in the recording, at least two propagation waves of uterine motion in at least two different regions of the uterus and/or on at least two different times; and determining 703 the degree of coordination of the uterine motion based on a similarity measure of at least two characteristics of the at least two propagation waves. The skilled person will readily understand how further steps may be added to the method. The device 710 illustrated in FIG. 7B comprises a processor 711 and a memory 712. The memory 712 may store instructions configured for, when executed on the processor 711, causing the processor 711 to perform the method according to any embodiment of the invention described herein.

It is noted that the above-described embodiments illustrate rather than limit the invention, and that the skilled person will be able to design numerous alternative embodiments.

In the claims, any reference signs placed between parentheses must not be construed as limiting the claim. Use of the verb "comprise" and its conjugations does not exclude the presence of elements or steps other than those stated in a claim. The article "a" or "an" preceding an element does not exclude the presence of a plurality of such elements. In the device, separate logical entities may be embodied by one and the same item of hardware. Features recited in mutually different dependent claims may advantageously combined where suitable.

The invention claimed is:

1. A computer-implemented image analysis method for quantitative assessment of a degree of coordination of uterine motion, comprising:
   receiving, by a processor, a digital recording of a uterus from an imaging modality selected from two-dimensional ultrasound, three-dimensional ultrasound, magnetic resonance imaging, or X-ray imaging;
   tracking, by the processor, in the recording, at least two propagation waves of uterine motion in at least two different regions of the uterus and/or on at least two different times;
   computing, by the processor, the degree of coordination of the uterine motion based on a similarity measure of at least two characteristics of the at least two propagation waves, wherein the degree of coordination relates to radial strain of at least the endometrium of the uterus; and
   outputting, by the processor, an indication of the degree of coordination.

2. The method of claim 1, wherein the processor computes at least two characteristics selected from the group consisting of: direction; dominant direction; velocity; amplitude; and phase.

3. The method of claim 1, wherein the method comprises:
   computing, by the processor, a measure of spread in the at least two characteristics over at least one of time and space using quantitative numerical metrics.

4. The method of claim 1, wherein the tracking comprises selecting tracing markers in the recording using semi-automatic computer assistance such that subsequent tracing markers are equidistant.

5. The method of claim 4, wherein the tracing markers are selected in accordance with an anatomical feature of the uterus.

6. The method of claim 5, wherein the tracing markers are along an anterior side and along a posterior side of the endometrium.

7. The method of claim 4, wherein the tracing markers are selected along an anterior side and along a posterior side of the endometrium.

8. The method of claim 1, comprising compensating motion of tracing markers by:
   selecting a set of tracing markers from among the tracing markers in a frame of the recording;
   determining a fitting curve based on the selected set of tracing markers;
   determining translation and rotation of the fitting curve;
   compensating coordinates of the tracing markers in subsequent frames of the recording based on the determined translation and rotation.

9. The method of claim 1, wherein the at least two propagation waves are tracked using any one of the following motion estimation techniques: block matching; optical flow; and optical flow including iterative spatial warping.

10. The method of claim 9, wherein the iterative spatial warping comprises combining optical flow from a current frame to a first frame later than the current frame with optical flow from the current frame to at least one second frame later than the first frame.

11. The method of claim 1, wherein the processor determines the similarity measure using one or more of the following similarity measures: cross correlation; coherence; mean square error; mutual information; and Hausdorff distance applied to tracked motion data extracted from the image recording.

12. The method of claim 1, further comprising:

representing the at least two propagation waves in a frequency domain;

determining a first sum of spectral energies from a first quartile of the at least two propagation waves represented in the frequency domain, as an energy of cervix-to-fundus propagation;

determining a second sum of spectral energies from a second quartile of the at least two propagation waves represented in the frequency domain, as an energy of fundus-to-cervix propagation; and based on the first sum and the second sum, determining a ratio of the cervix-to-fundus propagation to the fundus-to-cervix propagation in order to determine a dominant direction of the at least two propagation waves.

13. The method of claim 12, wherein the at least two propagation waves in a frequency domain are represented using a fast Fourier transform.

14. The method of claim 1, comprising:

determining whether or not the at least two propagation waves are symmetric regarding the at least two characteristics with respect to at least one symmetry axis of an anatomical feature of the uterus, preferably with respect to an endometrium of the uterus; and outputting result of the determining whether or not the at least two propagation waves are symmetric, as a measure for expected success of fertilization of the uterus.

15. The method of claim 1, comprising filtering out, with a bandpass filter, uterine motion components due to other sources than the uterus; wherein the other sources include at least one of: different organs than the uterus; and acquisition motion including any one or more of: a heartbeat; a respiration; and a recording probe movement.

16. The method of claim 1, wherein the recording is of any one of the following types: two-dimensional, 2D, ultrasound; three-dimensional, 3D, ultrasound; magnetic resonance; and X-ray imaging; and/or wherein the recording spans at least a time period of 20 seconds.

17. A non-transitory computer-readable medium storing instructions configured for, when executed on a processor, causing the processor to perform the method of claim 1.

18. Image analysis device for quantitative assessment of a degree of coordination of uterine motion, comprising a processor and a memory storing non-transitory instructions configured for, when executed on the processor, causing the processor to perform the method of claim 1.

19. The method of claim 1, wherein the recording is of any one of the following types: two-dimensional, 2D, ultrasound;

three-dimensional, 3D, ultrasound; magnetic resonance; and X-ray imaging; and/or wherein the recording spans at least a time period of 2 minutes.

20. The method of claim 1, wherein the recording is of any one of the following types: two-dimensional, 2D, ultrasound;

three-dimensional, 3D, ultrasound; magnetic resonance; and X-ray imaging; and/or wherein the recording spans at least a time period of 4 minutes.

* * * * *